United States Patent [19]

Dworkin et al.

[11] 4,032,552
[45] June 28, 1977

[54] ONE STEP METHOD FOR PREPARING NON-STOICHIOMETRIC DIORGANOTIN CARBOXYLATES USING A SOLID PHASE REACTION

[75] Inventors: Robert Dally Dworkin, Old Bridge; Adam Joseph Ejk, Piscataway, both of N.J.

[73] Assignee: M & T Chemicals Inc., Greenwich, Conn.

[22] Filed: June 12, 1975

[21] Appl. No.: 586,252

[52] U.S. Cl. .................... 260/414; 260/45.75 T; 260/429.7

[51] Int. Cl.² .................... C07F 7/22; C08K /00; C11C 1/00

[58] Field of Search .......... 260/429.7, 414, 45.75 T

[56] References Cited

UNITED STATES PATENTS

| | | | |
|---|---|---|---|
| 2,628,211 | 2/1953 | Mack et al. | 260/429.7 |
| 3,037,040 | 5/1962 | Anderson et al. | 260/429.7 |
| 3,418,349 | 12/1968 | Oakes | 260/429.7 |
| 3,458,472 | 7/1969 | Kauder et al. | 260/45.75 T |
| 3,463,751 | 8/1969 | Hasegawa et al. | 260/45.75 T |
| 3,476,786 | 11/1969 | Lally et al. | 260/414 |
| 3,511,803 | 5/1970 | Seki et al. | 260/45.75 T |
| 3,933,744 | 1/1976 | Coates et al. | 260/45.75 T |

FOREIGN PATENTS OR APPLICATIONS 1,913,284  7/1970  Germany .................... 260/414

Primary Examiner—Helen M. McCarthy
Attorney, Agent, or Firm—Robert P. Auber; Kenneth G. Wheeless; Robert Spector

[57] ABSTRACT

Diorganotin carboxylates containing more than 1 mole of tin for every 2 moles of carboxylic acid

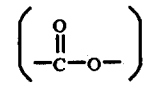

residues are prepared by a solid state reaction between a diorganotin oxide and a dicarboxylic acid anhydride. Depending upon the temperature of the oxide-anhydride mixture, the reaction is substantially complete in from less than 1 to up to 48 hours and produces no by-products.

6 Claims, No Drawings

ONE STEP METHOD FOR PREPARING NON-STOICHIOMETRIC DIORGANOTIN CARBOXYLATES USING A SOLID PHASE REACTION

BACKGROUND OF THE INVENTION

This invention relates to a method for preparing organotin compounds. The invention further relates to a method for preparing diorganotin carboxylates exhibiting reduced odor and fuming, particularly at elevated temperatures.

It is known that the so-called "non-stoichiometric" diorganotin derivatives of carboxylic acids containing more than 1 mole of tin for each mole of carboxylic acid residues are more stable than the corresponding stoichiometric compounds in that the odor of the carboxylic acid component is considerably less, especially at elevated temperatures. The property is particularly desirable for the diorganotin maleates, since the odor of maleic acid is very disagreeable in addition to being an irritant to the eyes and respiratory tract. U.S. Pat. No. 2,628,211 teaches the preparation of non-stoichiometric diorganotin carboxylates by "polymerization" of the corresponding stoichiometric compound obtained by reacting 1 mole of a diorganotin oxide for every 2 moles of a monocarboxylic acid or 1 mole of a dicarboxylic acid. The reaction is carried out in a liquid medium at elevated temperatures. "Polymerization" of the resultant stoichiometric compound is achieved by heating the compound in the presence of moisture. The degree of polymerization is dependent upon the specific reaction conditions employed. Some provision must be made for removing the free acid formed as a by-product of the reaction. The examples contained in the aforementioned patent employ a stream of moist air or steam for this purpose. Compounds containing more than three tin atoms per molecule are obtained by passing moist air through the reaction mixture for at least 6 hours, a costly and time-consuming procedure. Since the compound must remain in a reaction vessel throughout this treatment period, the process would not be commercially feasible since it would make only limited use of costly processing equipment, resulting in low volume efficiency in terms of amount of compound produced per unit time. This prior art method requires two steps, namely preparation of the "stoichiometric" diorganotin carboxylate and removal of the water produced as a by-product, followed by oligomerization of the carboxylate with concurrent removal of the by-product acid.

It has now been found that by using a solid acid anhydride instead of the corresponding carboxylic acid the relatively inefficient prior art method for preparing non-stoichiometric diorganotin carboxylates can be replaced by a one step method employing a solid phase reaction that does not generate any by-products. This process can be carried out with a minimum of residence time in the equipment used to blend the reagents.

SUMMARY OF THE INVENTION

The present invention provides a method for preparing non-stoichiometric diorganotin carboxylates exhibiting reduced odor, the method consisting essentially of maintaining an intimate, homogeneous mixture containing a particulate diorganotin oxide of the general formula $R_2^1$ SnO and a particulate, solid carboxylic acid anhydride exhibiting a formula selected from the group consisting of

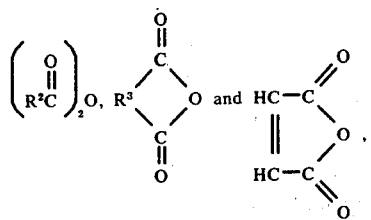

wherein between 1.1 and 6 moles of diorganotin oxide are present for each mode of said carboxylic acid anhydride, and allowing the resultant mixture to react for between about 24 and 48 hours at a temperature between ambient and 95° C. to form said diorganotin carboxylate in substantially quantitive yield. In the foregoing formulae $R^1$ represents an alkyl radical containing between 1 and 20 carbon atoms, a cycloalkyl, aryl, alkaryl or aralkyl radical wherein the alkyl residue of said alkaryl or aralkyl residue contains between 1 and 12 carbon atoms, $R^2$ represents an alkyl radical containing between 12 and 20 carbon atoms, an aryl, alkaryl or aralkyl radical wherein the alkyl residue of said alkaryl or aralkyl radical contains between 1 and 12 carbon atoms, $R^3$ is selected from the group consisting of alkylene radicals containing between 2 and 12 carbon atoms, 1,2-cycloalkenyl and o-phenylene radicals, wherein the carbon atoms of the $$-\overset{O}{\underset{\|}{C}}-O-\overset{O}{\underset{\|}{C}}-$$

radical are bonded to adjacent carbon atoms of said alkylene radical.

DETAILED DESCRIPTION OF THE INVENTION

In accordance with the present method finely divided particles of a diorganotin oxide are blended together with particles of a solid carboxylic acid anhydride to form a homogeneous mixture. The reagents are preferably combined at a temperature between ambient and 95° C. using high shear rates to obtain the desired uniformly small particle size range wherein the maximum particle size is 0.063 inch (0.16 cm.).

The reaction between the organotin oxide and the anhydride begins when the two reagents are placed in contact with one another and is complete for all practical purposes in from 24 to 48 hours at ambient temperature.

Alternatively, the oxide and anhydride can be individually ground to obtain the aforementioned particle size distribution. The finely divided reagents are then combined using any suitable mixing apparatus that will produce a homogeneous blend of two solid materials within a reasonably short time. This interval is usually between 5 and 60 minutes, depending upon the amount of material to be blended.

The present method employs between 1.1 and 6 moles of diorganotin oxide for every mole of acid anhydride. When the molar ratio of diorganotin oxide to acid anhydride exceeds 1:1 the characteristic odor of the stoichiometric diorganotin carboxylates disclosed in the prior art is eliminated or significantly reduced. This problem is particularly severe for diorganotin maleates, which are conventionally employed as heat stabilizers for halogen-containing polymers such as polyvinyl chloride. The stabilizer and any other additives are incorporated into a molten polymer using a roller mill, extruder or other suitable mixing apparatus wherein the temperature is maintained from 150° up to about 170° C. At these temperatures the odor of vaporized maleic anhydride generated by stoichiometric diorganotin maleates wherein the molar ratio of organotin oxide to anhydride is 1:1 or less is so irritating that respiratory masks, goggles and protective clothing must be worn by personnel in the area of the processing equipment. While the vapors of other solid carboxylic acid anhydrides may not be so irritating and hazardous as that of maleic anhydride, some provision must usually be made to remove these vapors by means of suitable blowers or fans.

While the present method preferably employs no more than 6 moles of diorganotin oxide per mole of acid anhydride, larger amounts of diorganotin compound can be reacted, depending upon the intended end use of the reaction product. For example, if the compound is to be used as a stabilizer for halogen-containing resins, the efficacy of the diorganotin carboxylate is significantly decreased when the molar ratio of diorganotin oxide to acid anhydride present in the compound exceeds about 6 to 1. for other end uses, including gel catalysts for preparing polyurethane, this effect is not apparent, and it may be desirable to employ relatively higher amounts of diorganotin oxide for the purpose of increasing the concentration of tin in the compound.

Any of the known diorganotin oxides are useful for preparing diorganotin carboxylates in accordance with the present method. The oxides can be represented by the formula $R_2^1 SnO$ wherein $R^1$ represents a monovalent hydrocarbon radical as previously defined. Those oxides not commercially available are readily prepared by hydrolysis of the corresponding diorganotin dihalide, which in turn can be obtained by reacting the corresponding tetraorganotin compound with stannic chloride or other stannic halide. The foregoing procedures have been described in the prior art, and do not form part of the present invention. If the diorganotin carboxylates are to be used as heat stabilizers for halogen-containing resins, $R^1$ is preferably methyl, butyl or octyl. Carboxylic acid anhydrides that are solid at ambient temperature include anhydrides of aliphatic monocarboxylic acids containing 10 or more carbon atoms, such as capric, hendecanoic, lauric, stearic and eicosanoic acids. Solid anhydrides of ethylenically unsaturated monocarboxylic acids such as oleic acid are also suitable, as are anhydrides derived from aromatic acids, including benzoic, salicylic and cinnamic acids. With few exceptions, the anhydrides of aliphatic, cycloaliphatic and aromatic dicarboxylic acids are solid materials at ambient temperature and would be useful in the present method. Known exceptions include dodecenylsuccinic and methyltetrahydrophthalic anhydrides.

If the maximum particle size of one or both of the oxide and acid anhydride exceeds the present limit of 0.063 inch, a satisfactory blending of the two reagents is readily achieved using a high speed, high shear mixer such as a Henschel or Waring blender. Under these conditions a homogeneous mixture of the desired particle size range is obtained in 5 minutes or less. The temperature in the mixing chamber may increase from ambient to 40° C. or higher during this time due to the heat generated by frictional forces. The walls of the mixing chamber are cooled or heated as required to maintain the temperature of the contents at between ambient and about 100° C.

Once an intimate mixture of the anhydride and diorganotin oxide is obtained, the product can be removed from the blending apparatus and packaged in suitable containers. As previously disclosed, it has been demonstrated that the reaction between the particles of anhydride and oxide continues following the actual blending operation and is substantially complete in between 24 and 48 hours at ambient temperature.

If shorter reaction times are desired the mixture of acid anhydride and diorganotin oxide can be heated to temperatures of 100° C. or higher. Preferably the mixture is tumbled or otherwise agitated to evenly distribute the heat.

The course of the reaction can readily be followed using infra-red spectroscopy. As the reaction proceeds the absorption maxima at 5.4 and 5.6 microns, which are characteristic of the

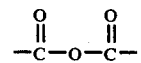

portion of the acid anhydride, gradually disappears and is replaced by absorption maxima at about 6.2 and 6.4 microns that are characteristic of the

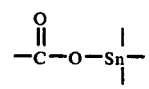

radical. Differential thermal analysis can also be used for this purpose.

The following examples disclose preferred embodiments of the present method and should therefore not be regarded as limiting the scope thereof either with regard to reagents or processing conditions.

EXAMPLE 1

This example demonstrates the preparation of non-stoichiometric or "overbased" dibutyltin maleate using the present method at ambient temperature. A mixture containing 2,506.2 g. (10.08 moles) of powdered dibutyltin oxide and 493.8 g. (5.04 moles) of maleic anhydride in the form of brickettes, measuring 1 1/2 by 1 inch (1.38 by 1.25 cm.), was placed in the mixing chamber of a Henschel blender equipped with two blades rotating on a common shaft and spaced about 0.5 inch (1.8 cm.) apart. The blades were rotated for 2 minutes at high speed (about 36,000 revolutions per minute) while the temperature within the mixing chamber was maintained below 45° C. by means of cooling water circulated within the wall of the chamber. The contents of the mixing chamber were then transferred to a container and remained at ambient temperature for about 40 hours, at which time a sample was analyzed using infra-red spectroscopy. No absorption maxima attributable to the original acid anhydride were observed. Absorption maxima at 6.2 and 6.4 microns established the presence of

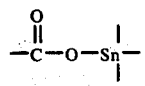

radicals.

EXAMPLE 2

Non-stoichiometric dibutyltin maleate (66.6 parts by weight) prepared as described in the first part of Example 1 was evaluated as a stabilizer for polyvinyl chloride in combination with stearic acid (26.7 parts) and 6.7 parts of 2,6-di-t-butyl-p-cresol. A stabilized polymer composition was prepared by combining 1.5 parts of this stabilizer formulation with 100 parts of a vinyl chloride homopolymer exhibiting an inherent viscosity of 0.97. The resultant mixture was placed on a two-roll differential speed mill heated to a temperature of 165° C. No appreciable odor of maleic acid could be detected from the heated mixture. The resultant polymer sheet was removed from the mill after 5 minutes and cut into test samples. The samples were placed in a circulating air oven heated to a temperature of 205° C. Samples were withdrawn at 5 minute intervals and rated for color using the Gardner color scale. The rate of darkening is a measure of the heat stability of the sample. The heat stability of these samples was only slightly inferior to samples containing an equal weight of a stoichiometric dibutyltin maleate prepared using equimolar amounts of dibutyltin oxide and maleic anhydride. A strong odor attributable to maleic anhydride evolved from the latter group of samples during processing.

EXAMPLE 3

This example demonstrates the reduction in reaction time that can be achieved using the present method at elevated temperature.

A mixture containing 747 g. (3 moles) of finely divided dibutyltin oxide and 147.5 g. (1.5 mole) of maleic anhydride was blended in a tumbling type mixing apparatus available as Twin-Shell Dry Blender Model 182181 from Paterson-Kelley Co. Inc. The mixing chamber was maintained at ambient temperature for 1 hour, at which time the walls of the mixing chamber were heated. At the end of 1 hour the temperature of the material in the chamber was 54° C. Differential thermal analysis of the material indicated that substantially all of it had reacted to form non-stoichiometric dibutyltin maleate. No significant change in the analysis was observed during 3 additional hours of heating.

EXAMPLE 4

A mixture containing 49.74 g. (0.2 mole) of dibutyltin oxide and 22.62 g. (0.1 mole) of benzoic anhydride was homogenized in a Waring Blender for 1 minute. The mixture was then allowed to remain at ambient temperature for about 3 weeks. During this time period virtially all the benzoic anhydride was consumed, as indicated by the disappearance of absorption maxima at 5.6 $\mu$ and 5.8 $\mu$. The appearance of absorption maxima at 6.3 $\mu$ and 6.5 $\mu$ demonstrated the presence of the

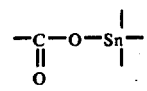

radicals that are characteristic of the desired product.

EXAMPLE 5

A mixture containing 49.74 g. (0.2 mole) of dibutyltin oxide and 55.10 g. (0.1 mole) of stearic anhydride was homogenized as described in Example 4. The reaction was virtually complete following heating of this mixture, as evidenced by the disappearance of absorption maxima at 5.55 $\mu$ and 5.65 $\mu$, characteristic of stearic anhydride, and the appearance of absorption maxima at 6.15 $\mu$ and 6.45 $\mu$, which are indicative of the organotin-carboxylate structure

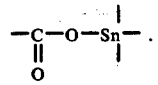

EXAMPLE 6

A mixture containing 99.48 g. (0.4 mole) of dibutyltin oxide and 29.62 g. (0.2 mole) of phthalic anhydride was homogeneously blended as disclosed in the preceding Example 4. An infrared spectrum obtained following 24 hours of heating at 65° C. exhibited no characteristic of the absorption maxima of phthalic anhydride (5.4 $\mu$ and 5.7 $\mu$). A broad absorption maximum at 6.3 $\mu$ indicated the presence of the organotin phthalate functional group,

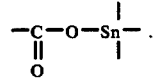

What is claimed is:
1. A method for preparing non-stoichiometric diorganotin carboxylates exhibiting reduced odor, said method employing a solid phase reaction that does not generate any by-products and consisting essentially of
   1. intimately blending a finely divided solid diorganotin oxide of the formula $R_2^1$ SnO and a finely divided solid carboxylic acid anhydride exhibiting a formula selected from the group consisting of

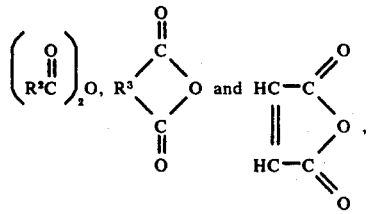

wherein the particle size of the diorgano tin oxide and carboxylic acid anhydride is uniformly small and does not exceed 0.063 inch (0.16 cm.) and wherein from 1.1 to 6 moles of said diorganotin oxide are present for every mole of said carboxylic acid anhydride;
   2. maintaining the temperature of the resultant mixture at between ambient and 100° C. for a period of time sufficient to form said non-stoichiometric diorganotin carboxylate; $R^1$ represents an alkyl radical containing between 1 and 20 carbon atoms, a cycloalkyl, aryl, alkaryl or aralkyl radical wherein the alkyl residue of said alkaryl or aralkyl residue contains between 1 and 12 carbon atoms, $R^2$ represents an alkyl radical containing between 12 and 20 carbon atoms, an aryl, alkaryl or aralkyl radical wherein the alkyl residue of said alkaryl or aralkyl radical contains between 1 and 12 carbon atoms, $R^3$ is selected from the group consisting of alkylene radicals containing between 2 and 12 carbon atoms, 1,2-cycloalkenyl and o-phenylene radicals, wherein the carbon atoms of the

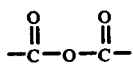

radical are bonded to adjacent carbon atoms of said alkylene radical.

2. The method of claim 1 wherein said mixture is reacted at ambient temperature.

3. The method of claim 1 wherein $R^1$ is a butyl radical.

4. The method of claim 1 wherein the carboxylic acid anhydride is maleic anhydride.

5. The method of claim 1 wherein $R^2$ represents a stearyl or a phenyl radical.

6. The method of claim 1 wherein $R^3$ represents an ethylene or an o-phenylene radical.

* * * * *